(12) United States Patent
Nacht

(10) Patent No.: US 12,029,811 B2
(45) Date of Patent: Jul. 9, 2024

(54) FORMULATION AND METHOD FOR THE TREATMENT OF ANDROGENIC ALOPECIA

(71) Applicant: CENTRO INTERNACIONAL DE COSMIATRÍA, S.A.P.I. DE C.V., Mexico City (MX)

(72) Inventor: Sergio Nacht, Las Vegas, NV (US)

(73) Assignee: CENTRO INTERNACIONAL DE COSMIATRÍA, S.A.P.I. DE C.V., Mexico City (MX)

( * ) Notice: Subject to any disclaimer, the term of this patent is extended or adjusted under 35 U.S.C. 154(b) by 67 days.

(21) Appl. No.: 16/968,018

(22) PCT Filed: Jan. 31, 2019

(86) PCT No.: PCT/MX2019/000008
§ 371 (c)(1),
(2) Date: Dec. 14, 2020

(87) PCT Pub. No.: WO2019/156545
PCT Pub. Date: Aug. 15, 2019

(65) Prior Publication Data
US 2021/0106519 A1   Apr. 15, 2021

(30) Foreign Application Priority Data
Feb. 6, 2018 (MX) .................. MX/A/2018/001546

(51) Int. Cl.
| | |
|---|---|
| A61K 9/00 | (2006.01) |
| A61K 31/07 | (2006.01) |
| A61K 31/506 | (2006.01) |
| A61K 31/58 | (2006.01) |
| A61K 47/10 | (2017.01) |
| A61K 47/22 | (2006.01) |
| A61K 47/32 | (2006.01) |
| A61K 47/34 | (2017.01) |

(52) U.S. Cl.
CPC ............ *A61K 9/0014* (2013.01); *A61K 31/07* (2013.01); *A61K 31/506* (2013.01); *A61K 31/58* (2013.01); *A61K 47/10* (2013.01); *A61K 47/22* (2013.01); *A61K 47/32* (2013.01); *A61K 47/34* (2013.01)

(58) Field of Classification Search
CPC ................. A61K 31/07; A61P 17/14
See application file for complete search history.

(56) References Cited

U.S. PATENT DOCUMENTS

| | | | | |
|---|---|---|---|---|
| 5,578,599 | A | * 11/1996 | Diani | ............ A61K 8/63 |
| | | | | 514/275 |
| 2004/0157766 | A1 | 8/2004 | Embil et al. | |
| 2005/0202049 | A1* | 9/2005 | Jentzsch | ............ A61Q 19/00 |
| | | | | 514/474 |
| 2011/0144141 | A1 | 6/2011 | Hu et al. | |
| 2011/0212167 | A1 | 9/2011 | Ali et al. | |
| 2015/0216986 | A1 | 8/2015 | Pohlmann et al. | |

FOREIGN PATENT DOCUMENTS

| | | | |
|---|---|---|---|
| CA | 2248496 A1 | * 4/1999 | |
| CN | 105106028 A | 12/2015 | |
| EP | 0 211 268 A2 | 2/1987 | |
| EP | 0306236 B1 | * 4/1993 | |
| WO | 2009/101497 A2 | 8/2009 | |
| WO | 2014/122436 A1 | 8/2014 | |
| WO | 2014/184173 A1 | 11/2014 | |
| WO | WO-2014184173 A1 | * 11/2014 | ........... A61K 8/4953 |

OTHER PUBLICATIONS

ISR for International Application PCT/MX2019/000008 and English Translation.
Written Opinion for International Application PCT/MX2019/000008 and English Translation.
CN 105106028 A_English Abstract.
Controlled release of benzoyl peroxide from a porous microsphere polymeric stem can reduce topical irritancy Wester et al. Journal of the American Academy of Dermatology vol. 24 pp. 720-726 (May 1991).
"The microsponge delivery system (MDS): a topical delivery system with reduced irritancy incorporating multiple triggering mechanisms for the release of actives", Embil et al.) in J.Microencapsulation, 1996 vol. 13 pp. 575-585.

* cited by examiner

*Primary Examiner* — Mark V Stevens
(74) *Attorney, Agent, or Firm* — LADAS & PARRY LLP

(57) ABSTRACT

The present invention relates to a topical formulation intended to be used for the treatment of androgenic or androgenetic baldness is men and women, with reduced side effects, especially with fewer collateral effects in the female population. The topical formulation comprises 0.01% to 10% by weight of Finasteride and a concentration of 1% to 5% by weight of Minoxidil in its free form or in an inert porous polymer. The combination of Finasteride and Minoxidil provides a synergistic effect against baldness. The formulation also comprises 0.15% by weight of retinol and is suitable for being applied to the scalp of the patient that requires it.

8 Claims, No Drawings

FORMULATION AND METHOD FOR THE TREATMENT OF ANDROGENIC ALOPECIA

RELATED APPLICATION

This application is a national phase entry under 35 USC 371 of International Patent Application No.: PCT/MX2019/000008 filed on 31 Jan. 2019, which claims priority from Mexican Application No. MX/a/2018/001546 filed on 6 Feb. 2018, the disclosures of which are incorporated in their entirety by reference herein.

FIELD OF THE INVENTION

The present invention relates to an effective formulation for the treatment of androgenic alopecia, specifically, the present invention is directed to a topical formulation for the treatment of androgenic alopecia in a subject in need thereof.

BACKGROUND OF THE INVENTION

Androgenic or androgenetic alopecia is one of the most common types of baldness among the world population that affects both the female and male population, with a higher rate of affection towards men. In men, androgenic alopecia is mediated by an increase in the secretion of testosterone (T) and its conversion by the enzyme 5a-reductase into dihydrotestosterone (DHT).

On the other hand, androgenic alopecia in women occurs by a similar process, particularly after menopause when the reduction in estrogens results in a hormonal imbalance with a preponderance of androgens, especially testosterone with its conversion to DHT. In women, hyperandrogenism can also occur as a result of a persistent syndrome of adrenarche that results in alopecia combined with facial hirsutism.

Currently the only compound available for the topical treatment of alopecia is Minoxidil which is used in a 5% solution to treat male alopecia or 2% to treat female alopecia. The therapeutic response is relatively satisfactory with a maximum of 40% of the individuals responding to the treatment.

In 1994, Merck introduced Finasteride under the name Prosear (in 5 mg tablets) for the oral treatment of benign prostatic hyperplasia and surprisingly discovered that in some of the patients hair began to grow. However, the side effects were significant, such as impotence, erection failure, decreased libido, and gynecomastia.

In addition, there is a risk that Finasteride may cause malformations in the fetus if used during pregnancy. As a consequence of the above, Merck reduced the dose to 1 mg daily and restricted the product to be used only in men. The United States Food and Drug Administration (FDA) approved in 1997 the use of oral Finasteride for the treatment of androgeretic alopecia in men that Merck introduced to the market under the name Propecia. This compound is an inhibitor of 5a: -reductase types II and III, which prevents the transformation of testosterone into DHT, significantly reducing the concentration of DHT in the scalp, although it does not completely prevent the formation of DHT and consequently has limited hormonal function.

Therefore, it would be desirable that Finasteride could be applied topically and penetrate the scalp at the level of the hair bulb in order to locally reduce the formation of DHT, allowing hair growth without producing undesirable systemic side effects, in particularly the teratogenesis. This occurs for example with retinoids (derived from Vitamin A) that, although they are administered orally in therapeutic concentrations, are also widely used topically without problems, especially retinol and trans-retinoic acid.

Minoxidil, the only drug that is used topically for the treatment of alopecia, has a mechanism of action that is not fully clarified, although it is postulated that it works by producing local vasodilation and opening the cellular potassium channels. This allows the blood to containing oxygen and nutritional elements, it reaches the hair follicle more easily, stimulating it to the anagen or growth phase and developing thicker and longer hair.

In the state of the art there are some documents that describe the use of Finasteride in some product that is applied to the scalp for the treatment of androgenic alopecia, such as U.S. Pat. No. 6,908,889 B2 that describes a composition that is useful as shampoo, gel, bath cream, lotion or mousse to clean the skin, hair and/or nails and with the aim of deposition of a thin coating to condition the hair fibers, treat hair loss, promote the growth of hair, among other benefits unrelated to alopecia. Said patent mentions a composition that can include between 0.001-20% of an agent, said agent being Finasteride. However, said patent does not mention a combination of Finasteride with Minoxidil that provides an improved effect as claimed in the present invention.

SUMMARY OF THE INVENTION

The present invention aims to provide a topical formulation for the treatment of androgenic alopecia, said formulation comprising a concentration of Finasteride in combination with concentrations of different silicones and a concentration of Minoxidil. The formulation being useful for the treatment and inhibition of alopecia in both men and women with a minimum of side effects on the subject using the formulation of the present invention. The present invention further provides a safer and more efficient formulation compared to what is known in the state of the art.

DETAILED DESCRIPTION OF THE INVENTION

In the present invention, the term androgenic alopecia or androgenetic alopecia will be used to refer to the same condition. For practical purposes of the present description, N-(1,1-dimethylethyl)-3-oxo-4-aza 5a-androst-1-en-17β-carboxamide will be referred to by its name Finasteride, while 2,6-diamino-4-(piperidin-1-yl) pyrimidine 1-oxide will be referred to as Minoxidil.

Finasteride (CAS No. 98319-26-7; Molecular Weight: 372.5) is a medium-sized, highly lipophilic, corticoid-like molecule that requires appropriate carriers for the formulation of a topical product that results in trans-epidermal penetration of the drug in sufficient quantities to stimulate the hair follicle, but minimizing systemic penetration that could result in any undesirable side effects. Therefore, transdermal penetration in amounts that stimulate the hair follicle without the side effects would allow Finasteride to also be used in women without the danger of teratogenesis, and in men would significantly reduce side effects.

For this, the Applicant has developed an anhydrous vehicle specially formulated with silicones that can dissolve Finasteride and promote its transcutaneous penetration when applied topically. These vehicles are also useful for the transport of other substances that promote hair growth by providing nourishing elements for hair formation. The formulation is reinforced by the inclusion of Minoxidil since this compound acts by a mechanism other than Finasteride and therefore the stimulation of hair growth is additive and synergistic.

The formulation consists of a concentration from 0.01% to 10% of Finasteride, and more preferably in a concentration of 1% to 2% and in a concentration of from 1% to 5% of Minoxidil, and more preferably 2%. The present formulation also includes various silicones, such as, but not limited to, Dimethicone, Dimethicone Crospolymer, Cyclopentasiloxane, among others in different concentrations. Additionally, the formulation may comprise a concentration of pure retinol or retinol in acrylate crosspolymers in a concentration from 0.05% to 0.5% by weight, and more preferably 0.15% by weight. It should be noted that the tables indicated are exemplary and not limiting.

EXAMPLES OF FORMULATIONS

Formula 1

TABLE 1

Example of Formula 1 for hair growth

| Ingredient | % in weight |
|---|---|
| Finasteride | 1.00 |
| Minoxidil | 2.00 |
| Retinol | 0.15 |
| Tetrahexadecyl Ascorbate | 0.50 |
| Ascorbic acid | 0.50 |
| Dl-alpha-toeopheryl acetate | 0.05 |
| Phitantriol | 1.00 |
| C12-15 Alkyl Benzoate | 1.90 |
| B HT | 0.05 |
| Polydimethyl syloxane | 3.50 |
| Cyclopentasiloxane & Crospolymer Dimethicone c.s.p. | 100.00 |

Formula 2

TABLE 2

Example of Formula 2 for hair growth

| Ingredient | % in weight |
|---|---|
| Finasteride | 1.00* |
| Minoxidil | 2.00* |
| Retinol | 0.15* |
| Tetrahexadecyl Ascorbate | 0.50 |
| Ascorbic acid | 0.50 |
| Dl-alpha-toeopheryl acetate | 0.05 |
| Phitantriol | 1.00 |
| C12-15 Alkyl Benzoate | 1.90 |
| B HT | 0.05 |
| Crospelymer of methyl methacryiate and EGDMA | 7.50** |
| Polydimethyl syloxane | 3.50 |
| Cyclopentasiioxane | 15.00 |
| Cyclopentasiloxane & Crospolymer Dimethicone c.s.p. | 100.00 |

*These ingredients are added to the formulation pre-incorporated in a methacrylate crospolymer to obtain a slow and prolonged release when the product is applied to the scalp.
**An allyl methacrylate crospolymer or other suitable monomers such as styrene and divinylbenzene can also be used.

Based on tables 1 and 2 which refer to alternative formulas for hair growth, it can be noted that both formulas contain the sane active ingredients at the sane concentration, but in Formula I the Finasteride and Minoxidil are freely dispersed in the vehicle of the base formula, while in Formula II these actives and Retinol are previously incorporated into an inert porous polymer such as methyl methacrylate crossed with EGDMA (ethylene glycol dimethacrylate) as a "carrier". These polymers with the different active ingredients are then incorporated into the base formula. In this way, when the final formulation is applied to the scalp, a slow and prolonged release of the main ingredients is obtained that reduces the potential for skin irritation and increases the effectiveness of the formulation, allowing a better dosage of the active ingredients.

Clinical Efficacy Study

Here are the results of a clinical study that demonstrates the safety and efficacy of four different: formulations. The study was conducted using four different formulations, which are:

Formula A: It is the complete formula 1 or 2, but without the Minoxidil or the Finasteride.
Formula B: It is Formula A with the addition of only Minoxidil.
Formula C: It is Formula A plus the Minoxidil and Finasteride freely dispersed in the vehicle.
Formula D: It is the same Formula C but with the Minoxidil and Finasteride pre-incorporated in an inert polymer.

Study Design:

The four formulations were studied in groups of 5 volunteers each over 30 years of age, including in each group at least two women.

Volunteers were instructed to apply the assigned product to the entire scalp twice daily, specifically in the morning and evening. In each case, they were instructed to apply the formulation approximately 20 or 30 minutes after washing their hair.

In each case, they were instructed to apply the formulation approximately 20 or 30 minutes after washing their hair.

Participants were given a neutral shampoo without conditioners and instructed to return after 4, 6, 8 and 12 weeks of use.

At each visit, the safety and efficacy of the treatment was evaluated using the following hair presence scale:
0: Nothing or absence.
1: Mild
2: Moderate
3: Strong (safety) or very good (efficacy)
4: Very strong (safety) or excellent (efficacy)

In each case, the reported values represent the total for each group

Results:
Safety Assessment

TABLE 3

Results of the clinical study of hair growth (efficacy)

| WEEK | 4 | 6 | 8 | 12 |
|---|---|---|---|---|
| Side effect: erythema | | | | |
| Formula A | 0 | 0 | 0 | 0 |
| Formula B | 0 | 0 | 0 | 0 |
| Formula C | 0 | 0 | 0 | 0 |
| Formula D | 0 | 0 | 0 | 0 |
| Side effect: Burning | | | | |
| Formula A | 1 | 0 | 0 | 0 |
| Formula B | 3 | 5 | 0 | 0 |

TABLE 3-continued

Results of the clinical study of hair growth (efficacy)

| WEEK | 4 | 6 | 8 | 12 |
|---|---|---|---|---|
| Formula C | 4 | 6 | 6 | 5 |
| Formula D | 1 | 2 | 1 | 0 |
| Side effect: Itching | | | | |
| Formula A | 1 | 0 | 0 | 0 |
| Formula B | 3 | 2 | 1 | 1 |
| Formula C | 4 | 6 | 4 | 3 |
| Formula D | 1 | 3 | 1 | 0 |

Efficacy Evaluations

TABLE 4

Results of the hair growth clinical study (efficacy)

| WEEK | 4 | 6 | 8 | 12 |
|---|---|---|---|---|
| New hair growth | | | | |
| Formula A | 0 | 5 | 7 | 8 |
| Formula B | 2 | 5 | 8 | 11 |
| Formula C | 5 | 10 | 16 | 18 |
| Formula D | 8 | 14 | 18 | 20 |
| Smoother hair | | | | |
| Formula A | 5 | 5 | 10 | 12 |
| Formula B | 5 | 7 | 10 | 13 |
| Formula C | 5 | 8 | 11 | 13 |
| Formula D | 7 | 9 | 12 | 14 |
| Brighter hair | | | | |
| Formula A | 7 | 10 | 10 | 10 |
| Formula B | 9 | 8 | 10 | 12 |
| Formula C | 8 | 11 | 14 | 15 |
| Formula D | 8 | 12 | 14 | 15 |

Tables 3 and 4 present the results obtained in the safety and efficacy evaluations and are presented as the sum of the "scores" or individual scores in each group.

The results of the safety evaluations are presented in Table 3 and indicate that the four formulas are safe for the indicated use.

Slight burning and itching is observed, particularly with Formula C which contains all active materials incorporated freely in the vehicle. On the other hand, when the active ingredients are previously incorporated into porous polymeric structures capable of producing a slow release, these effects decrease significantly and tolerance increases.

Table 4 presents the efficacy data obtained in the study. Their analysis clearly indicates that Formula A has a slight effect on hair growth, probably due to its content of Vitamins (A, C and E) and Fitantriol (derived from Vitamin A). When Minoxidil (Formula B) is added there is a significant increase in efficacy, as expected. However, surprisingly the addition of Finasteride topically increased efficacy much more in all participants, particularly when the actives are incorporated in polymeric structures. In particular, faster growth was observed when Finasteride and Minoxidil were included both free and in polymers.

All of the formulas mentioned in the present invention had acceptable cosmetic properties possibly due to the hair softening effects of the silicones used as the base. Likewise, these compounds increase the shine of the hair as is known. Unexpectedly, it was observed that the incorporation of Minoxidil and Finasteride also increased the cosmetic properties of the hair.

CONCLUSION

The clinical study conducted clearly demonstrates that:
1. An anhydrous silicone-based formulation with the addition of Minoxidil is effective in stimulating hair growth in both men and women.
2. When Finasteride is added to these formulations, the efficacy is significantly increased, both in the speed of efficacy and in the amount of hair that grows.
3. If Minoxidil and Finasteride are previously incorporated into porous polymeric structures to obtain a slow and prolonged release of these active ingredients, an increase in efficacy and a redaction of possible side effects such as burning and itching of the skin are observed.
4. All formulations used are safe for topical use, in particular those containing the active ingredients.
5. All of these formulations are cosmetically acceptable and improve the properties of the hair, especially its softness and shine.

It is noted that in relation to this date, the best method known by the applicant to put the aforementioned invention into practice, is the one that is clear from the present description of the invention.

The invention claimed is:

1. A method for treatment of androgenic baldness and/or in promoting hair growth in a subject in need thereof, the method consisting of administering a topical formulation comprising a combination of finasteride in a concentration from 1% to 5% by weight, a concentration of minoxidil from 1% to 5% by weight, and a concentration of retinol in acrylate crosspolymers from 0.05% to 1% by weight, wherein the finasteride, the minoxidil, and the retinol in acrylate crosspolymers are incorporated in a slow releasing inert porous polymer, wherein the inert porous polymer is a methyl methacrylate crosslinked with ethylene glycol dimethacrylate in a concentration of 7.50% by weight.

2. The method of claim 1, wherein the finasteride is in a concentration of 1% by weight.

3. The method of claim 1, wherein the minoxidil is in a concentration of 2% by weight.

4. A method for treatment of androgenic baldness and/or in promoting hair growth in a subject in need thereof, the method consisting of administering a topical formulation comprising a combination of finasteride in a concentration from 1% to 5% by weight, a concentration of minoxidil from 1% to 5% by weight, and a concentration of retinol in acrylate crosspolymers from 0.05% to 1% by weight, wherein the finasteride, the minoxidil and retinol in acrylate crosspolymers are incorporated in a slow releasing inert porous polymer, wherein the inert porous polymer is an allyl methacrylate crosspolymer or a styrene/divinylbenzene crosspolymer.

5. The method of claim 1, wherein the retinol in acrylate crosspolymers is in a concentration of 0.15% by weight.

6. The method of claim 1, wherein the formulation is administered from 4 to 12 weeks, twice a day.

7. The method of claim 4, wherein the retinol in acrylate crosspolymers is in a concentration of 0.15% by weight.

8. The method of claim 4, wherein the formulation is administered from 4 to 12 weeks, twice a day.

* * * * *